United States Patent [19]

Wariishi

[11] Patent Number: 5,728,832
[45] Date of Patent: Mar. 17, 1998

[54] PHTHALIDE COMPOUND AND RECORDING MATERIAL USING THE SAME

[75] Inventor: Koji Wariishi, Minami-ashigara, Japan

[73] Assignee: Fuji Photo Film Co., Ltd., Kanagawa, Japan

[21] Appl. No.: 734,953

[22] Filed: Oct. 23, 1996

[30] Foreign Application Priority Data

Oct. 23, 1995 [JP] Japan ................... 7-273984

[51] Int. Cl.$^6$ .................. C10M 105/72; C07D 239/00
[52] U.S. Cl. ............................... 544/249; 252/47
[58] Field of Search ................... 544/249; 252/47

[56] References Cited

U.S. PATENT DOCUMENTS

| | | | |
|---|---|---|---|
| 4,224,071 | 9/1980 | Buell | 106/22 |
| 4,328,223 | 5/1982 | Kabbe et al. | 424/246 |
| 5,097,029 | 3/1992 | Shannon | 544/249 |
| 5,147,568 | 9/1992 | Luzzi et al. | 252/47 |
| 5,563,144 | 10/1996 | Damour et al. | 514/253 |

FOREIGN PATENT DOCUMENTS

| | | |
|---|---|---|
| 58-5940 | 2/1983 | Japan . |
| 62-243653 | 10/1987 | Japan . |
| 2138368 | 5/1990 | Japan . |
| 5212958 | 8/1993 | Japan . |

OTHER PUBLICATIONS

Gleiter et. al., "Electronic Structure of Heterospireness . . . ", J. Org. Chem., 1986, vol. 51, pp. 370–380.

Wasulko et. al., "Synthesis of Potential Antineoplastic Agents . . . " J. Med. Chem., Jul. 1966, vol. 9, No. 4, pp. 599–601.

*Primary Examiner*—Mukund J. Shah
*Assistant Examiner*—Tamthom T. Ngo
*Attorney, Agent, or Firm*—Birch, Stewart, Kolasch & Birch, LLP

[57] ABSTRACT

A phthalide compound represented by formula (I) and a recording material containing the phthalide compound:

wherein Ar represents a substituent represented by one of formulas (II-1), (II-2) and (III), and the other symbols in formula (I) are defined in the specification:

20 Claims, No Drawings

PHTHALIDE COMPOUND AND RECORDING MATERIAL USING THE SAME

FIELD OF THE INVENTION

The present invention relates to a phthalide compound for use in a color former for recording materials such as pressure-sensitive paper and heat-sensitive paper. More specifically, the present invention relates to a novel near infrared-absorbing phthalide compound capable of providing a color image which can be read by an optical character reader. The present invention further relates to a recording material using the compound.

BACKGROUND OF THE INVENTION

Phthalide compounds are well known as a color former for recording materials such as pressure-sensitive paper, heat-sensitive paper, photosensitive pressure-sensitive paper and electric heat-sensitive recording paper.

In recent years, use of an optical character reader (e.g., OCR, OMR) using near infrared rays and use of a bar-code reader are increasing, and development of a color former having an absorption in a near infrared region so as to be used in recording materials for these devices is demanded.

However, colored images formed from a conventional phthalide compound typically including crystal violet lactone has no or almost no absorption in the near infrared region, and therefore the images are unsuitable to be read with the optical character reader.

Accordingly, various phthalide compounds as a color former having absorption in the near infrared region have been proposed, for example, in JP-A-5-212958 (the term "JP-A" as used herein means an "unexamined, published Japanese patent application"), JP-A-2-138368, JP-A-62-243653 and JP-B-58-5940 (the term "JP-B" as used herein means an "examined Japanese patent publication").

However, any of these compounds is a compound having one or two vinyl groups. Accordingly, incorporation of the vinyl group is accompanied by complicatedness in the synthesis route, increase of the number of processing steps and rise of costs in the industrial production.

SUMMARY OF THE INVENTION

An object of the present invention is to provide a novel color former for recording materials, which requires no introduction of a vinyl group, is easily synthesized and provides a colored image having intense absorption in the near infrared region.

Another object of the present invention is to provide a recording material suitable for use with an image reader equipped with an easily available means (light source) such as a semiconductor laser.

The above-described objects of the present invention have been achieved by providing:

(1) a phthalide compound represented by formula (I):

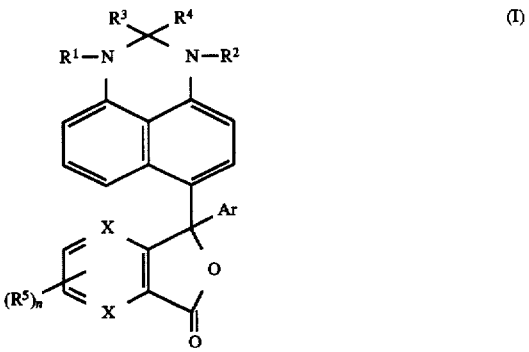

wherein $R^1$, $R^2$, $R^3$ and $R^4$ each represents a hydrogen atom, an alkyl group or an aryl group, $R^5$ represents a hydrogen atom, a halogen atom, a dialkylamino group or a carboxyl group, X represents a group of CH or a nitrogen atom, $R^3$ and $R^4$ may be bonded with each other to form a 5- or 6-membered ring, Ar represents a substituent represented by one of formulas (II-1), (II-2) and (III), n represents an integer of from 1 to 4, provided that when n is 2 or greater, a plurality of $R^5$ groups may be the same or different:

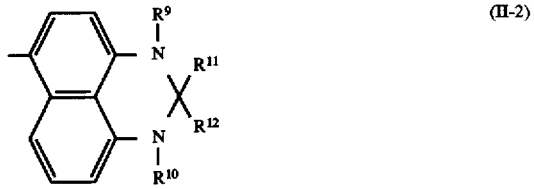

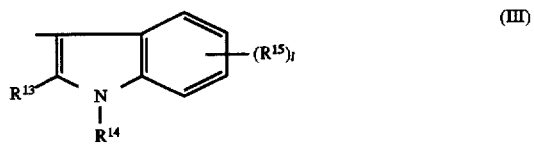

wherein $R^6$ and $R^7$ each represents an alkyl group or an aryl group, $R^6$ and $R^7$ may be bonded with each other to form a 5- or 6-membered ring, $R^8$ represents a hydrogen atom, an alkyl group, an aryl group, an alkoxy group, an amino group, a hydroxyl group or a halogen atom, m represents an integer of from 1 to 4, provided that when m is 2 or greater, a plurality of $R^8$ groups may be the same or different, $R^9$, $R^{10}$, $R^{11}$ and $R^{12}$ each represents a hydrogen atom, an alkyl group or an aryl group, $R^{11}$ and $R^{12}$ may be bonded with each other to form a 5- or 6-membered ring, $R^{13}$ and $R^{14}$ each represents a hydrogen atom, an alkyl group or an aryl group, $R^{15}$ represents a hydrogen atom, an alkyl group, an alkoxy group, an amino group or a hydroxy group, and l represents an integer of from 1 to 4, provided that when l is 2 or greater, a plurality of $R^{15}$ groups may be the same or different.

(2) a recording material containing a phthalide compound represented by formula (I).

DETAILED DESCRIPTION OF THE INVENTION

Formula (I) is described in detail below.

The alkyl group represented by each of $R^1$, $R^2$, $R^3$ and $R^4$ is a linear, branched or cyclic alkyl group, and examples thereof include methyl, ethyl, propyl, n-butyl, sec-butyl, t-butyl, isobutyl, n-pentyl, n-hexyl, cyclohexyl, 2-ethylhexyl and cyclopentyl. The alkyl group may have a substituent such as a hydroxyl group, an alkoxy group having from 1 to 8 carbon atoms, a cyano group and a halogen atom. The alkyl group is preferably an alkyl group having from 1 to 10 carbon atoms, more preferably a linear or branched alkyl group having from 1 to 10 carbon atoms.

The aryl group represented by each of $R^1$, $R^2$, $R^3$ and $R^4$ is preferably an aryl group having from 6 to 10 carbon atoms. The aryl group may have a substituent. Examples of the substituent include an alkyl group having from 1 to 4 carbon atoms (e.g., methyl, ethyl, t-butyl and n-propyl), a halogen atom (e.g., fluorine, chlorine, bromine and iodine), a cyano group, an alkoxy group having from 1 to 8 carbon atoms (e.g., methoxy and ethoxy), an aryloxy group having from 6 to 10 carbon atoms (e.g., phenoxy and naphthoxy), a carboxyl group, an ester group having from 2 to 8 carbon atoms (e.g., methoxycarbonyl and ethoxycarbonyl), a carbamoyl group having from 1 to 8 carbon atoms (e.g., dimethylcarbamoyl and diethylcarbamoyl), an alkylsulfonyl group having from 1 to 8 carbon atoms (e.g., methylsulfonyl), an acylamino group having from 2 to 8 carbon atoms (e.g., acetylamino and propionylamino), an acyl group having from 2 to 8 carbon atoms (e.g., acetyl and propionyl), a urethane group having from 2 to 8 carbon atoms (e.g., methoxycarbonylamino and n-butoxycarbonylamino), a ureido group having from 1 to 8 carbon atoms (e.g., methylcarbamoylamino and phenylcarbamoylamino), a sulfamoyl group having from 0 to 8 carbon atoms (e.g., methylsulfamoyl and ethylsulfamoyl), a sulfo group, a hydroxyl group and a substituted amino group such as dimethylamino group. The aryl group is more preferably a substituted or unsubstituted phenyl group, still more preferably an unsubstituted phenyl group.

Examples of the 5- or 6-membered ring formed by bonding $R^3$ and $R^4$ with each other include cyclopentyl and cyclohexyl.

Examples of the halogen atom represented by $R^5$ include chlorine, fluorine, bromine and iodine, with a chlorine atom being preferred.

The dialkylamino group represented by $R^5$ is preferably a dialkylamino group having from 2 to 16 carbon atoms such as dimethylamino, diethylamino and dibutylamino, more preferably a dialkylamino group having from 2 to 12 carbon atoms, still more preferably a dialkylamino group having from 2 to 8 carbon atoms.

The alkyl group represented by each of $R^6$ and $R^7$ has the same meaning as the alkyl group represented by each of $R^1$, $R^2$, $R^3$ and $R^4$.

The aryl group represented by each of $R^6$ and $R^7$ has the same meaning as the aryl group represented by each of $R^1$, $R^2$, $R^3$ and $R^4$.

Examples of the 5- or 6-membered ring formed by bonding $R^6$ and $R^7$ with each other include pyrrolidino and piperidino.

The alkyl group and the aryl group represented by $R^8$ have the same meaning as the alkyl group and the aryl group represented by each of $R^6$ and $R^7$, respectively.

The alkoxy group represented by $R^8$ is preferably a substituted or unsubstituted alkoxy group having from 1 to 8 carbon atoms such as methoxy, ethoxy, butoxy and methoxyethoxy, more preferably an unsubstituted alkoxy group, still more preferably an unsubstituted alkoxy group having from 1 to 6 carbon atoms.

The amino group represented by $R^8$ is preferably a substituted or unsubstituted amino group having from 0 to 8 carbon atoms. Examples of the preferred amino group include amino, methylamino, dimethylamino, diethylamino, phenylamino, methoxyphenylamino, chlorophenylamino, morpholino, piperidino, pyrrolidino, pyridylamino, methoxycarbonylamino, butoxycarbonylamino, phenoxycarbonylamino, methylcarbamoylamino, phenylcarbamoylamino, acetylamino, ethylcarbonylamino, cyclohexylcarbonylamino, benzoylamino, chloroacetylamino and methylsulfonylamino. The amino group is more preferably a substituted amino group, still more preferably a dialkylamino group.

Examples of the halogen atom represented by $R^8$ include fluorine, chlorine, bromine and iodine. Of these, fluorine, chlorine and bromine are preferred, and chlorine and bromine are more preferred.

The alkyl group and the aryl group represented by each of $R^9$, $R^{10}$, $R^{11}$ and $R^{12}$ have the same meaning as the alkyl group and the aryl group represented by each of $R^1$, $R^2$, $R^3$ and $R^7$, respectively.

Examples of the 5- or 6-membered ring formed by bonding $R^{11}$ and $R^{12}$ with each other include cyclopentyl and cyclohexyl.

The alkyl group represented by each of $R^{13}$ and $R^{14}$ is preferably a substituted or unsubstituted alkyl group having from 1 to 12 carbon atoms, and examples thereof include methyl, ethyl, propyl, isopropyl, n-butyl, isobutyl, sec-butyl, t-butyl, methoxyethyl, ethoxyethyl, ethoxycarbonylmethyl, ethoxycarbonylethyl, cyanoethyl, diethylaminoethyl, hydroxyethyl, chloroethyl and acetoxyethyl. The alkyl group is more preferably an unsubstituted alkyl group, still more preferably an unsubstituted alkyl group having from 1 to 6 carbon atoms.

The aryl group represented by each of $R^{13}$ and $R^{14}$ is preferably a substituted or unsubstituted aryl group having from 6 to 10 carbon atoms, and examples thereof include phenyl, naphthyl, tolyl, chlorophenyl and methoxyphenyl. The aryl group is more preferably a substituted or unsubstituted phenyl group, still more preferably an unsubstituted phenyl group.

The alkyl group, the alkoxy group and the amino group represented by $R^{15}$ have the same meaning as the alkyl group, the alkoxy group and the amino group represented by $R^8$, respectively.

Specific examples of the phthalide compound represented by formula (I) of the present invention are shown below, but the compound is not limited to these examples.

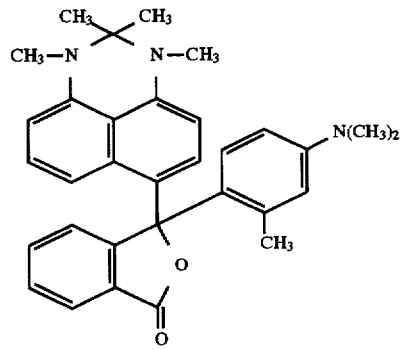

I-1.

-continued
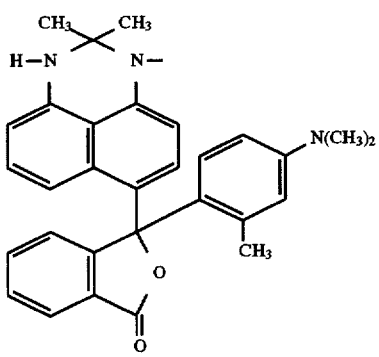
I-2.
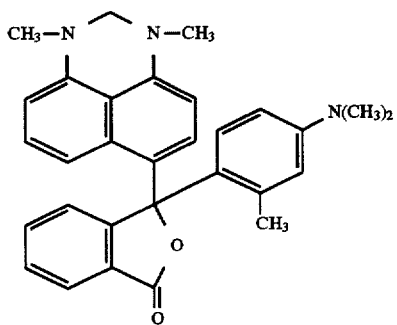
I-3.
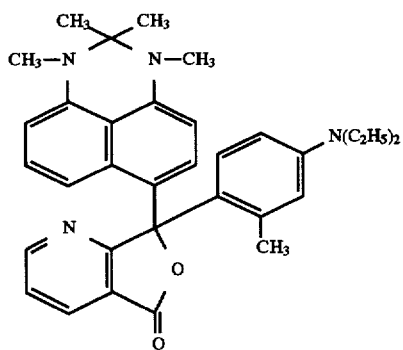
I-4.
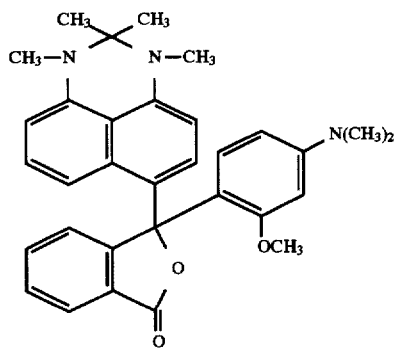
I-5.
-continued
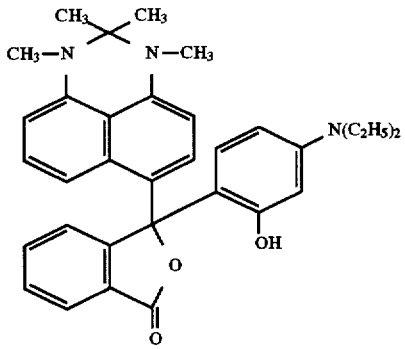
I-6.
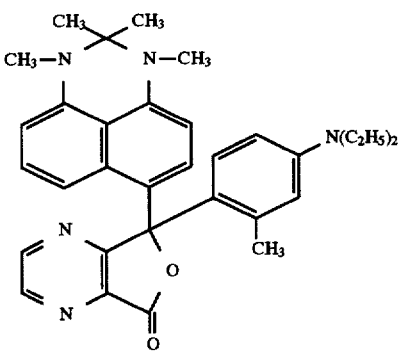
I-7.
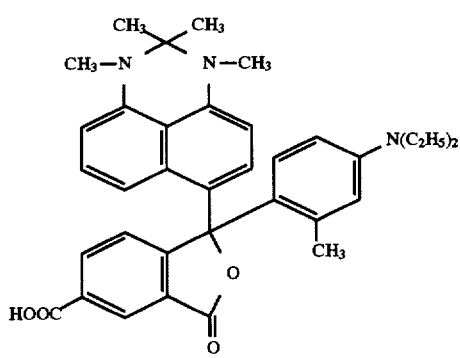
I-8.
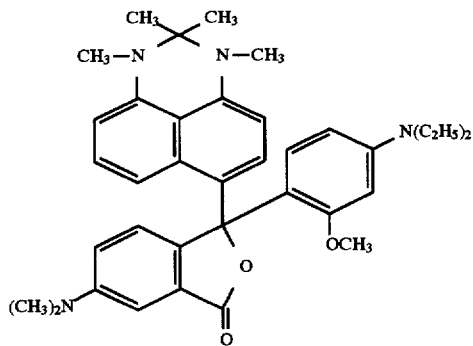
I-9.

-continued
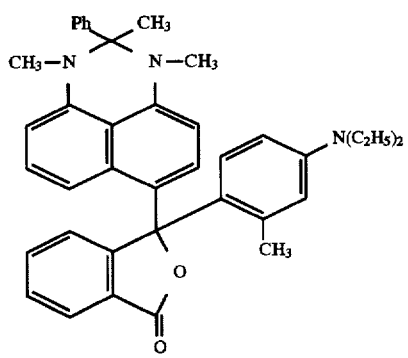
I-10.
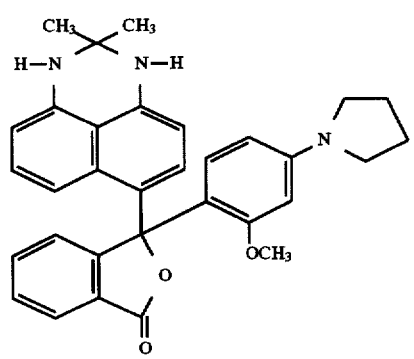
I-11.
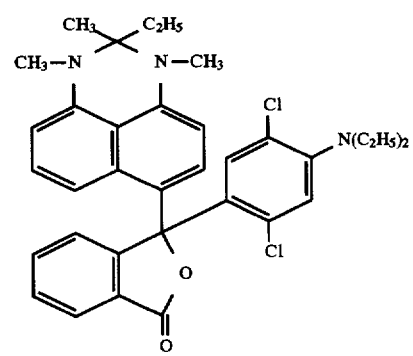
I-12.
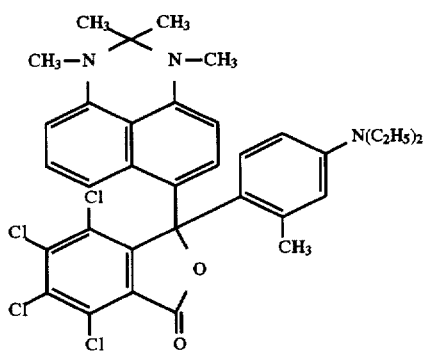
I-13.
-continued
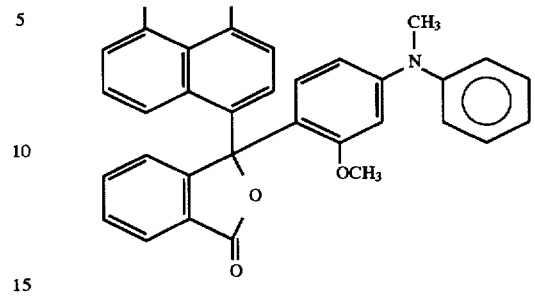
I-14.
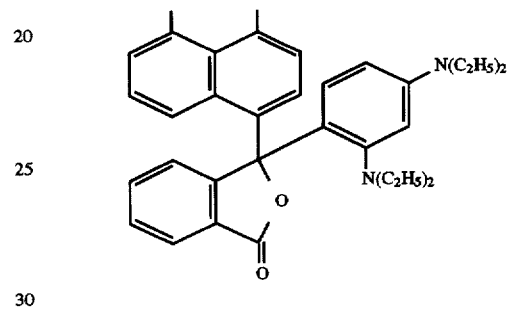
I-15.
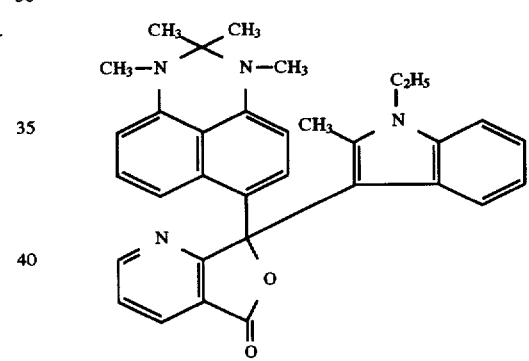
I-16.
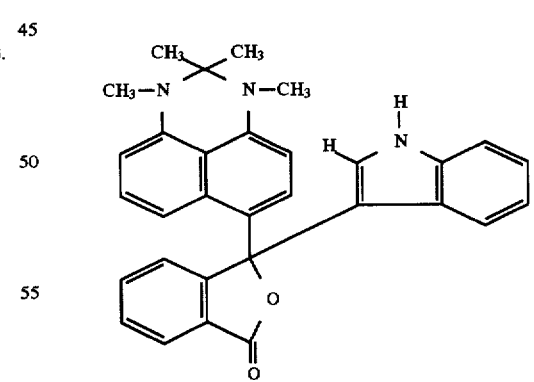
I-17.

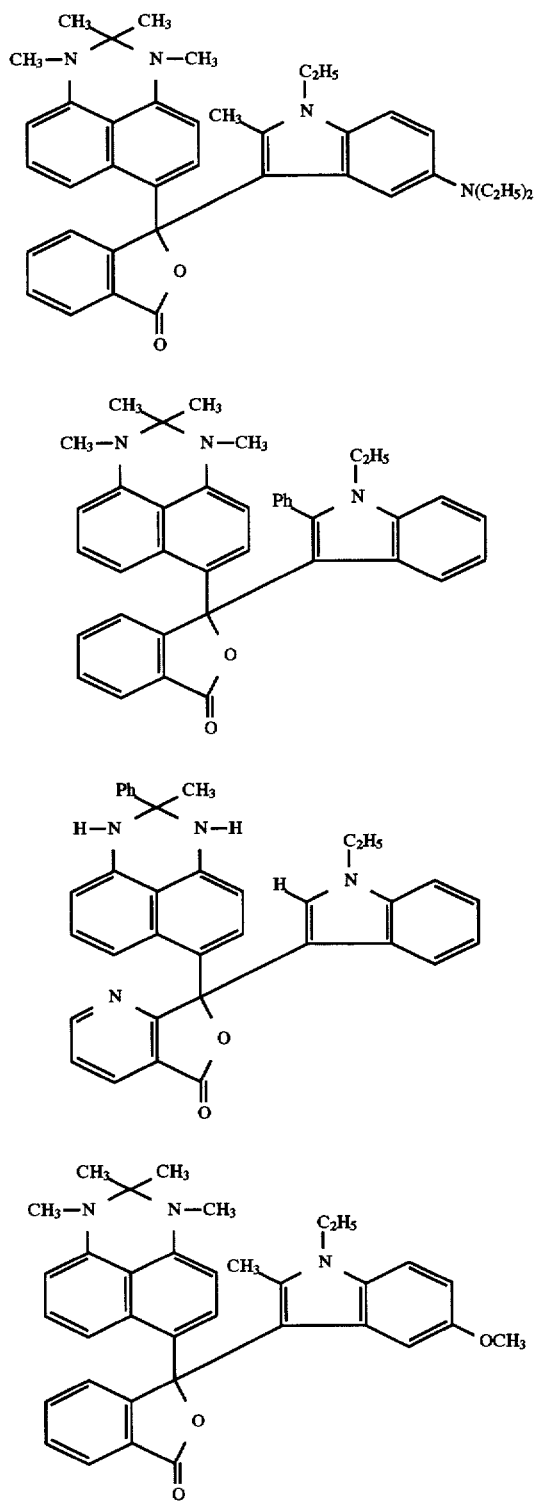
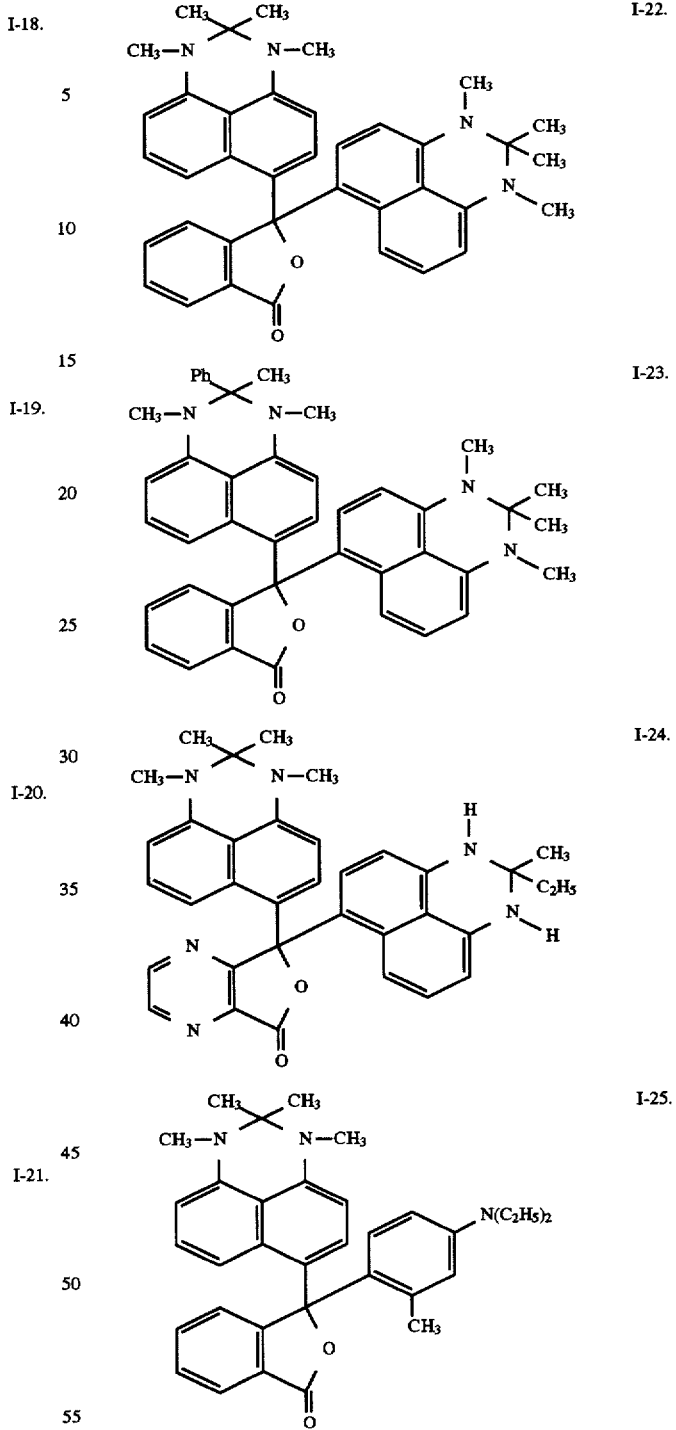
The phthalide compound represented by formula (I) is a novel compound, however, it can be synthesized by a known method. For example, the phthalide compound dan be easily synthesized by a dehydration condensation reaction of a ketocarboxylic acid represented by formula (IV-1) corresponding to objective compound with an aniline compound represented by formula (V-1), a diaminonaphthalene compound represented by formula (V-2) or an indole compound represented by formula (V-3); or by that of a ketocarboxylic acid represented by formula (IV-2) corresponding to objective compound with a diaminonaphthalene compound represented by formula (V-4):

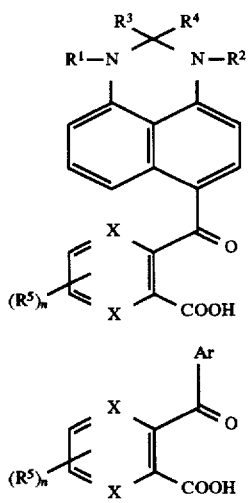

wherein $R^1$, $R^2$, $R^3$, $R^4$, $R^5$, X, Ar and n have the same meaning as those in formula (I);

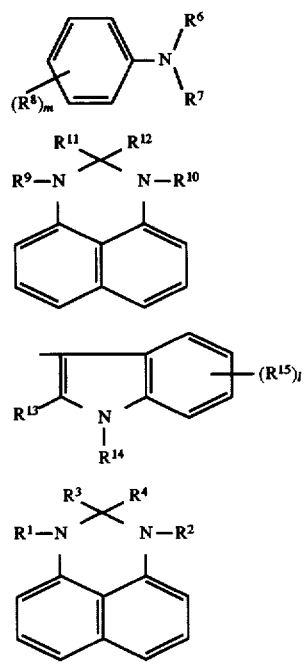

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, l and m have the same meaning as those in formula (I).

The ketocarboxylic acid represented by formula (IV-1) as used herein can be obtained by reacting an acid anhydride represented by formula (VI) with a compound represented by formula (V-4) in an organic inactive solvent such-as benzene, toluene, tetrachloroethane, chlorobenzene or nitrobenzene, or by reacting them using a Lewis acid capable of activating Friedel-Crafts reaction such as aluminum chloride and zinc chloride, and similarly, the ketocarboxylic acid of formula (IV-2) can be obtained from an acid anhydride of formula (VI) with a compound represented by one of formulas (V-1) to (V-3):

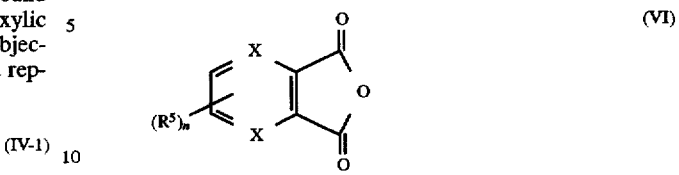

wherein X, $R^5$ and n have the same meaning as those in formula (I).

Examples of the condensing agent for use in this reaction include acetic anhydride, sulfuric aid, polyphosphoric acid, phosphorus oxychloride and zinc chloride. The reaction is generally performed at a temperature of from 10° to 150° C.

Specifically, the synthesis can be performed according to JP-A-2-101075.

The phthalide compound represented by formula (I) of the present invention, which can be obtained as described above, is usually a colorless or slightly colored compound and provides very excellent effects when it is used various recording materials which utilizes a color reaction with an electron-accepting substance (hereinafter referred to as a developer).

Useful examples of the developer used here include acidic clay-base developers (e.g., clay, bentonite and activated clay), phenol/formaldehyde resins (e.g., p-phenylphenol/formaldehyde resin), metal salts of a salicylic acid compound (e.g., zinc 3,5-bis-α-methylbenzylsalicylate), phenol/salicylic acid/formaldehyde resins (e.g., p-octylphenol/zinc salicylate/formaldehyde resin), zinc rhodanide and zinc xanthate, and in addition, compounds having an active hydrogen such as phenol compounds, pyrazolone compounds and sulfonamide compounds are also preferably used.

The phthalide compound of the present invention can be used, similarly to conventional phthalide compounds, as a color former of recording materials such as pressure-sensitive recording material, heat-sensitive recording material and thermal transfer-type recording material.

In producing a pressure-sensitive recording material using the phthalide compound of the present invention, microcapsules containing the phthalide compound dissolved in an organic solvent are prepared. The microcapsule is prepared by a method described, for example, in U.S. Pat. No. 2,800,457, where diisopropylnaphthalene-base oil or terphenyl-base oil having dissolved therein from 1 to 10% of the phthalide compound is encapsulated into an outer shell wall formed by hardening gelatin or a resin such as melamine-formalin. The size of the microcapsule is usually about 5 μm. The microcapsules are placed on a support such as paper or a plastic film, using a binder to obtain a color former-containing sheet. The thus-prepared color former-containing sheet is superposed on a developer-containing sheet having a layer containing a developer (electron accepting compound), and capsules are ruptured by applying thereon a pressure such as pressure by pencil. Then the phthalide compound comes into contact with the developer, thereby forming a color image on the developer-containing sheet.

In producing a heat-sensitive recording material using the phthalide compound of the present invention, the phthalide compound, a developer (electron accepting compound) and an auxiliary component such as a filler are dispersed in an aqueous medium, and the mixture is coated together with a binder on a support and dried. In this case, the size of the phthalide compound is suitably approximately from 0.1 to 5 μm. The obtained heat-sensitive recording material is heated by a thermal head to melt the phthalide compound to come into melt-contact with the developer, thereby obtaining a colored image.

In producing a heat transfer-type recording material using the phthalide compound of the present invention, the phthalide compound is disposed on a support in the same manner as described above to prepare a heat transfer sheet. Separately, a developer is also held on a support in the same manner as above to form an image-receiving sheet. The thus prepared transfer sheet and the image-receiving sheet are superposed and heated from the surface of the transfer sheet to obtain a colored image on the image-receiving sheet.

The phthalide compound of the present invention may be used in various fields similarly to conventional ones. Particularly, it can be used as a color former of recording materials for an optical character reader or for record reader such as label bar coder and bar code reader, by virtue of its excellent near-infrared-absorbing property.

When the phthalide compound of the present invention is used in a heat-sensitive recording label sheet, the structure of the sheet may be such that a heat-sensitive coloring layer containing the phthalide compound of the present invention and a developer is provided on one side of a support, and a release layer is provided on another side of the support via an adhesive layer. In this case, if desired, a protective layer such as a water-soluble resin layer may be provided on the surface of the heat-sensitive coloring layer so as to increase the image stability.

The present invention will be described in more detail below with reference to the following Examples, but the invention should not be construed as being limited thereto. Unless otherwise indicated, the "parts" and "%" in Examples are both by weight.

EXAMPLE 1

Synthesis of Compound I-25:

To a mixture of 3.1 g of Compound (a) and 10 ml of acetic anhydride, 2.3 g of Compound (b) was added and the mixture was stirred at room temperature for 3 hours. To the reaction solution, 20 ml of methanol was added, and the crystals were filtered, washed with 20 ml of methanol and dried. Yield: 2.5 g.

Compound (a):

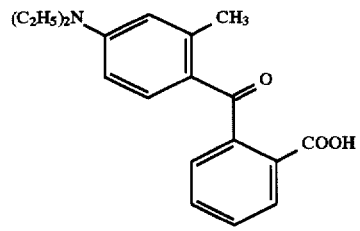

Compound (b):

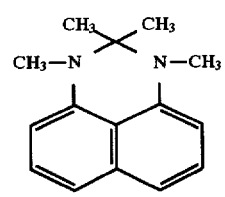

EXAMPLE 2

Synthesis of Compound I-16:

To a mixture of 6.2 g of Compound (c) and 20 ml of acetic anhydride, 4.5 g of Compound (b) was added and the mixture was stirred at room temperature for 3 hours. To the reaction solution, 20 ml of ethyl acetate was added, and the crystals were filtered, washed with 20 ml of methanol and dried. Yield: 8.7 g.

Compound (c):

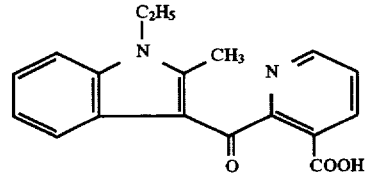

EXAMPLE 3

(Preparation of Pressure-sensitive Sheet)
Preparation of Color Former-containing Capsule Sheet:

To 95 parts of hot water at about 80° C., 5 parts of a partially sodium salt of polyvinylbenzenesulfonic acid (trade name: VERSA TL500, average molecular weight: 500,000, produced by National-Starch K.K.) was added while stirring. The sodium salt was dissolved over about 30 minutes and then the solution was cooled. The aqueous solution had a pH of from 2 to 3 and thereto a 20 wt % sodium hydroxide was added to adjust the pH to 4.0.

On the other hand, 100 parts of diisopropylnaphthalene having dissolved therein 3.5% of phthalide compound I-25 (color former) of the present invention was emulsion-dispersed in 100 parts of a 5% aqueous solution of the above-described partially sodium salt of polyvinylbenzenesulfonic acid to obtain an emulsion solution having an average oil droplet size of 4.5 μm.

Separately, 6 parts of melamine, 11 parts of a 37 wt % formaldehyde aqueous solution and 30 parts of water were stirred under heating at 60° C. and after 30 minutes, a transparent mixed aqueous solution of the initial condensate of melamine, formaldehyde and melamine formaldehyde (hereinafter referred to as an "initial condensate solution") was obtained. This mixed aqueous solution had a pH of from 6 to 8.

The resulting initial condensate solution was added to and mixed with the above prepared emulsion solution and the pH thereof was adjusted to 6.0 by adding thereto a 3.6 wt % phosphoric acid solution while stirring. The solution temperature was raised to 65° C. and stirring was continued for 6 hours to obtain a microcapsule dispersion solution. The resulting capsule solution was cooled to room temperature and the pH thereof was adjusted to 9.0 with 20 wt % sodium hydroxide.

To this capsule dispersion solution, 200 parts of a 10 wt % polyvinyl alcohol aqueous solution (trade name: PVA-117, produced by Kuraray Co., Ltd.) and 50 parts of starch particles were added, and then water was added thereto to obtain a coating solution having a solid concentration of 20%. Then, the resulting coating solution was coated on a base paper having a weight of 50 g/m² by an air knife coater so as to have a solid coating content of 5 g/m², and then dried to obtain a color former-containing capsule sheet (hereinafter referred to simply as a "color former sheet").

Preparation of Developer Sheet:
To 20 parts of 1-isopropylphenyl-2-phenylethane, 10 parts of zinc 3,5-bis-α-methylbenzylsalicylate was added and dissolved under heating at 90° C. The resulting mixture was added to 50 parts of an aqueous solution of a 2 wt % polyvinyl alcohol (trade name: PVA-117, produced by Kuraray Co., Ltd.) and further thereto 0.1 part of an aqueous solution of a 10% dodecylbenzenesulfonic acid triethanolamine salt was added to prepare an emulsion solution having an average oil droplet size of 3 μm using a homogenizer.

Then, 80 parts of calcium carbonate, 20 parts of zinc oxide, 1 part of sodium hexametaphosphate and 200 parts of water were dispersed by a Kady mill to prepare a dispersion solution. The solution was mixed with the above prepared emulsion solution, and added thereto 100 parts of a 10 wt % polyvinyl alcohol (trade name: PVA-117, produced by Kuraray Co., Ltd.) as a binder and 10 parts of a carboxy-modified SBR latex (trade name: Nogatex SN-307, produced by Sumitomo Naugatuck Company, Ltd.) as a solid content. To the mixture, water was added to have a solid concentration of 20% to prepare Coating Solution (A).

Separately, using 15 parts of zinc 3,5-bis-α-methylbenzylsalicylate, 20 parts of silt clay, 60 pats of calcium carbonate, 20 parts of zinc oxide, 1 part of sodium hexametaphosphate and 200 parts of water, a dispersion solution having an average grain size of 3 μm was prepared by a sand grinder.

To the resulting dispersion solution, 16 parts of a 10 wt % polyvinyl alcohol aqueous solution (trade name: PVA-103, produced by Kuraray Co., Ltd.) was added, and then 100 parts of a 10 wt % polyvinyl alcohol (trade name: PVA-117, produced by Kuraray Co., Ltd.) and 10 parts of a carboxy-modified SBR latex (trade name: Nogatex SN-307, produced by Sumitomo Naugatuck Company, Ltd.) as a solid content were added thereto. To the mixture, water was added to prepare Coating Solution (B) having a solid content concentration of 20%.

Coating Solution (A) and Coating Solution (B) were mixed at a (A)/(B) ratio, in terms of a developer, of 50/50 and coated on a base paper having a weight of 50 g/m² by an air knife coater so as to have a solid coating content of 5.0 g/m², and then dried to prepare a developer-containing sheet (hereinafter simply referred to as a "developer sheet").

The above prepared developer sheet and the color former sheet were combined to prepare Pressure-Sensitive Sheet (I).

EXAMPLE 4

Pressure-sensitive recording sheet (II) was prepared in the same manner as in Example 3 except for using phthalide compound I-16 in place of phthalide compound I-25 used in the preparation of a color former sheet in Example 3.

COMPARATIVE EXAMPLE 1

Pressure-sensitive recording sheet (III) was prepared in the same manner as in Example 3 except for using crystal violet lactone (CVL) in place of phthalide compound I-25 used in the preparation of a color former sheet in Example 3.

CVL:

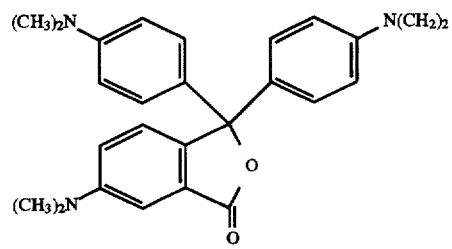

Evaluation as a Pressure-sensitive Sheet:

On each of pressure-sensitive recording sheets (I) to (III) prepared above, a pressure was applied. Then, a color image having a high density according to respective color formers was obtained. The tone and the absorption wavelength region on absorption spectrum of each sample are shown in Table 1, in which λmax represents peak absorption wavelength.

TABLE 1

| Pressure-sensitive Recording Sheet | Phthalide Compound | Color Hue | Absorption Wavelength Region (nm) | Remarks | |
|---|---|---|---|---|---|
| I | I-25 | blue green | 650–950 | (λmax 716) | Invention |
| II | I-16 | blue green | 600–900 | (λmax 681) | " |
| III | CVL | blue | 550–640 | (λmax 610) | Comparison |

As is apparent from the results in Table 1, color images obtained from pressure-sensitive recording sheets (I) and (II), in which the phthalide compound of the present invention was used, exhibited strong light absorption with respect to the wavelength in the near infrared region, whereas color image obtained from pressure-sensitive recording sheet (III) using a known phthalide compound exhibited almost no light absorption with respect to the wavelength in the near infrared region.

According to the present invention, a novel phthalide compound which gives a colored product having absorption in the near infrared region and can be easily synthesized is provided. Further, a recording material which can be used for an image reader having a light source of near infrared region is provided.

While the invention has been described in detail and with reference to specific examples thereof, it will be apparent to one skilled in the art that various changes and modifications can be made therein without departing from the spirit and scope thereof.

What is claimed is:

1. A phthalide compound represented by formula (I):

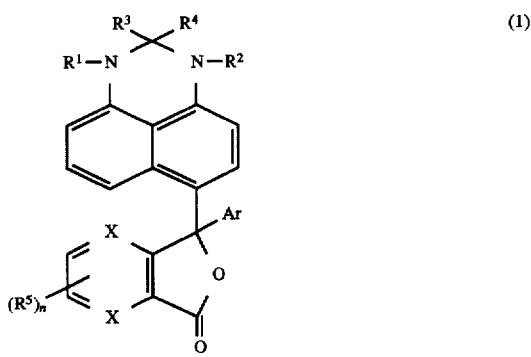

wherein $R^1$, $R^2$, $R^3$ and $R^4$ each represents a hydrogen atom, an alkyl group or an aryl group, $R^5$ represents a hydrogen atom, a halogen atom, a dialkylamino group or a carboxyl group, X represents a group of CH or a nitrogen atom, $R^3$ and $R^4$ may be bonded with each other to form a 5- or 6-membered ring, n represents an integer of from 1 to 4, provided that when n is 2 or greater, the $R^5$ groups may be the same or different, Ar represents a substituent represented by one of formulas (II-1), (II-2) and (III):

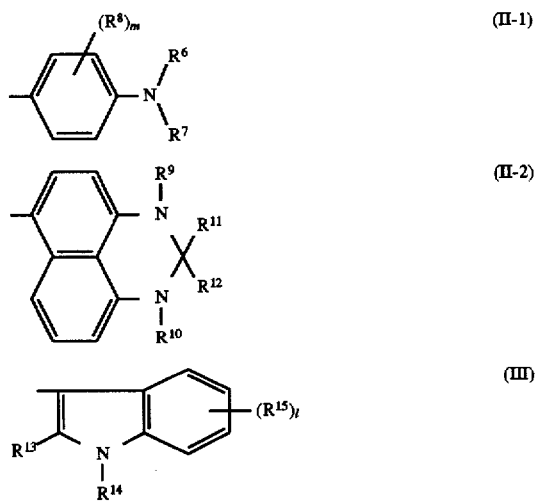

wherein $R^6$ and $R^7$ each represents an alkyl group or an aryl group, $R^6$ and $R^7$ may be bonded with each other to form a 5-or 6-membered ring, $R^8$ represents a hydrogen atom, an alkyl group, an aryl group, an alkoxy group, an amino group, a hydroxyl group or a halogen atom, m represents an integer of from 1 to 4, provided that when m is 2 or greater, the $R^8$ groups may be the same or different, $R^9$, $R^{10}$, $R^{11}$ and $R^{12}$ each represents a hydrogen atom, an alkyl group or an aryl group, $R^{11}$ and $R^{12}$ may be bonded with each other to form a 5- or 6-membered ring, $R^{13}$ and $R^{14}$ each represents a hydrogen atom, an alkyl group or an aryl group, $R^{15}$ represents a hydrogen atom, an alkyl group, an alkoxy group, an amino group or a hydroxy group, and l represents an integer of from 1 to 4, provided that when l is 2 or greater, the $R^{15}$ groups may be the same or different.

2. A phthalide compound according to claim 1, wherein the alkyl group represented by each of $R^1$, $R^2$, $R^3$, $R^4$, $R^6$, $R^7$, $R^8$, $R^9$, $R^{10}$, $R^{11}$, $R^{12}$ and $R^{15}$ contains a substituent selected from the group consisting of hydroxyl, $C_{1-8}$ alkoxy, cyano and halogen.

3. A phthalide compound according to claim 1, wherein the alkyl group represented by each of $R^1$, $R^2$, $R^3$, $R^4$, $R^6$, $R^7$, $R^8$, $R^9$, $R^{10}$, $R^{11}$, $R^{12}$ and $R^{15}$ is selected from the group consisting of linear alkyl, branched alkyl and cyclic alkyl.

4. A phthalide compound according to claim 3, wherein the alkyl group represented by each of $R^1$, $R^2$, $R^3$, $R^4$, $R^6$, $R^7$, $R^8$, $R^9$, $R^{10}$, $R^{11}$, $R^{12}$ and $R^{15}$ is selected from the group consisting of methyl, ethyl, propyl, n-butyl, sec-butyl, t-butyl, isobutyl, n-pentyl, n-hexyl, cyclohexyl, 2-ethylhexyl and cyclopentyl.

5. A phthalide compound according to claim 1, wherein the alkyl group represented by each of $R^1$, $R^2$, $R^3$, $R^4$, $R^6$, $R^7$, $R^8$, $R^9$, $R^{10}$, $R^{11}$, $R^{12}$ and $R^{15}$ is a $C_{1-10}$ alkyl group.

6. A phthalide compound according to claim 1, wherein the aryl group represented by each of $R^1$, $R^2$, $R^3$, $R^4$, $R^6$, $R^7$, $R^8$, $R^9$, $R^{10}$, $R^{11}$ and $R^{12}$ contains a substituent selected from the group consisting of $C_{1-4}$ alkyl, halogen, cyano, $C_{6-10}$ aryloxy, carboxyl, $C_{2-8}$ ester, $C_{1-8}$ carbamoyl, $C_{1-8}$ alkylsulfonyl, $C_{2-8}$ acylamino, $C_{2-8}$ acyl, $C_{2-8}$ urethane, $C_{1-8}$ ureido, $C_{0-8}$ sulfamoyl, sulfo, hydroxyl, and substituted amino.

7. A phthalide compound according to claim 1, wherein the aryl group represented by each of $R^1$, $R^2$, $R^3$, $R^4$, $R^6$, $R^7$, $R^8$, $R^9$, $R^{10}$, $R^{11}$ and $R^{12}$ is a $C_{6-10}$ aryl group.

8. A phthalide compound according to claim 7, wherein the $C_{6-10}$ aryl group is an unsubstituted phenyl group.

9. A phthalide compound according to claim 1, wherein the 5- or 6-membered ring formed by bonding $R^3$ and $R^4$ with each other is selected from the group consisting of cyclopentyl and cyclohexyl.

10. A phthalide compound according to claim 1, wherein the dialkylamino group represented by $R^5$ is a dialkylamino group having from 2 to 16 carbon atoms.

11. A phthalide compound according to claim 10, wherein the $C_{2-16}$ dialkylamino group is selected from the group consisting of dimethylamino, diethylamino and dibutylamino.

12. A phthalide compound according to claim 1, wherein the 5- or 6-membered ring formed by bonding $R^6$ and $R^7$ with each other is selected from the group consisting of pyrrolidino and piperidino.

13. A phthalide compound according to claim 1, wherein the alkoxy group represented by each of $R^8$ and $R^{15}$ is a substituted or unsubstituted alkoxy group having from 1 to 8 carbon atoms.

14. A phthalide compound according to claim 13, wherein the alkoxy group is selected from the group consisting of methoxy, ethoxy, butoxy and methoxyethoxy.

15. A phthalide compound according to claim 1, wherein the amino group represented by each of $R^8$ and $R^{15}$ is a substituted or an unsubstituted amino group.

16. A phthalide compound according to claim 15, wherein the amino group is selected from the group consisting of amino, methyl amino, dimethylamino, diethylamino, phenylamino, methoxyphenylamino, chlorophenylamino, morpholino, piperido, pyrrolidino, pyridylamino, methoxycarbonylamino, butoxycarbonylamino, phenoxycarbonylamino, methylcarbamoylamino, phenylcarbamoylamino, acetylamino, ethylcarbonylamino, cyclohexylcarbonylamino, benzoylamino, chloroacetylamino and methylsulfonylamino.

17. A phthalide compound according to claim 1, wherein the 5- or 6-membered ring formed by bonding $R^{11}$ and R12 with each other is selected from the group consisting of cyclopentyl and cyclohexyl.

18. A phthalide compound according to claim 1, wherein the alkyl group represented by each of $R^{13}$ and $R^{14}$ is an alkyl group having from 1 to 6 carbon atoms.

19. A phthalide compound according to claim 1, wherein the aryl group represented by each of $R^{13}$ and $R^{14}$ is a phenyl group.

20. A recording material comprising a phthalide compound represented by formula (I):

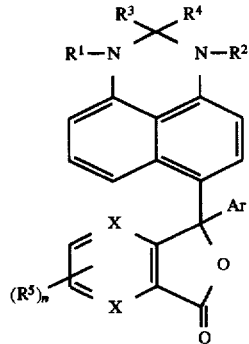
(I)

wherein $R^1$, $R^2$, $R^3$ and $R^4$ each represents a hydrogen atom, an alkyl group or an aryl group, $R^5$ represents a hydrogen atom, a halogen atom, a dialkylamino group or a carboxyl group, X represents a group of CH or a nitrogen atom, $R^3$ and $R^4$ may be bonded with each other to form a 5- to 6-membered ring, n represents an integer of from 1 to 4, provided that when n is 2 or greater, the $R^5$ groups may be the same or different, Ar represents a substituent represented by one of formulas (II-1), (II-2) and (III):

(II-1)

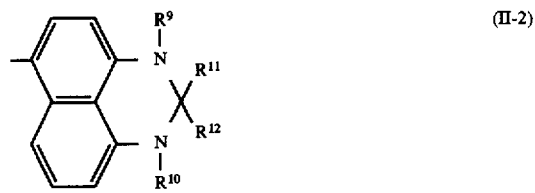
(II-2)

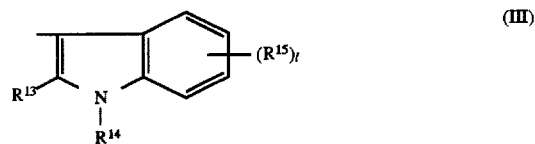
(III)

wherein $R^6$ and $R^7$ each represents an alkyl group or an aryl group, $R^6$ and $R^7$ may be bonded with each other to form a 5- or 6-membered ring, $R^8$ represents a hydrogen atom, an alkyl group, an aryl group, an alkoxy group, an amino group, a hydroxyl group or a halogen atom, m represents an integer of from 1 to 4, provided that when m is 2 or greater, the $R^8$ groups may be the same or different, $R^9$, $R^{10}$, $R^{11}$ and $R^{12}$ each represents a hydrogen atom, an alkyl group or an aryl group, $R^{11}$ and $R^{12}$ may be bonded with each other to form a 5- or 6-membered ring, $R^{13}$ and $R^{14}$ each represents a hydrogen atom, an alkyl group or an aryl group, $R^{15}$ represents a hydrogen atom, an alkyl group, an alkoxy group, an amino group or a hydroxy group, and l represents an integer of from 1 to 4, provided that when l is 2 or greater, the $R^{15}$ groups may be the same or different.

* * * * *